US012733815B2

(12) United States Patent
Son et al.

(10) Patent No.: US 12,733,815 B2
(45) Date of Patent: Sep. 15, 2026

(54) ORAL DIAGNOSTIC DEVICE USING LIGHT

(71) Applicant: SMARTOOTH CO., LTD., Seoul (KR)

(72) Inventors: Ho Jung Son, Seoul (KR); Myung Seon Ryou, Seoul (KR)

(73) Assignee: SMARTOOTH CO., LTD., Seoul (KR)

( * ) Notice: Subject to any disclaimer, the term of this patent is extended or adjusted under 35 U.S.C. 154(b) by 48 days.

(21) Appl. No.: 18/789,117

(22) Filed: Jul. 30, 2024

(65) Prior Publication Data

US 2025/0120590 A1 Apr. 17, 2025

(30) Foreign Application Priority Data

Oct. 17, 2023 (KR) ........................ 10-2023-0138287

(51) Int. Cl.
*A61B 5/00* (2006.01)

(52) U.S. Cl.
CPC .................................. *A61B 5/0088* (2013.01)

(58) Field of Classification Search
CPC ....... A61B 5/0088; A61B 1/24; A61B 5/4547; A61B 5/0062; A61B 5/0071; A61B 6/51; A61C 9/0053; A61C 19/04; A61C 1/088; A61C 9/0046
USPC ........................................................... 433/29
See application file for complete search history.

(56) References Cited

U.S. PATENT DOCUMENTS 5,993,378 A * 11/1999 Lemelson ......... A61M 25/0069 600/109
6,053,731 A * 4/2000 Heckenberger ...... A61B 5/0088 433/29
6,118,521 A * 9/2000 Jung ....................... G01J 3/508 356/417
6,590,665 B2 * 7/2003 Painchaud ............. G01D 5/268 356/477
7,404,929 B2 * 7/2008 Fulghum, Jr. ...... G01N 21/6486 422/82.05

(Continued)

FOREIGN PATENT DOCUMENTS

AU 8380298 A * 1/1999 ............. G01N 21/00
CA 2613074 A1 * 1/2007 ........... A61C 19/004

(Continued)

*Primary Examiner* — Matthew M Nelson
(74) *Attorney, Agent, or Firm* — United One Law Group LLC; Kongsik Kim; Jhongwoo Peck

(57) ABSTRACT

An oral diagnostic device includes a device main body including an optical transmitting and receiving module; and a probe that is detachably coupled to the device main body, irradiates light received from the optical transmitting and receiving module into an oral cavity, receives reflected light from the oral cavity, and transmits the received reflected light to the optical transmitting and receiving device. The optical transmitting and receiving module includes an optical element module including a light-emitting element and a light-receiving element, a single first optical fiber that transmits the light generated by the light-emitting element to the probe, and a plurality of second optical fibers that transmit the reflected light received from the probe to the light-receiving element. The single first optical fiber and the plurality of second optical fibers are coupled to each other at the other sides thereof to form an optical fiber coupling part.

9 Claims, 10 Drawing Sheets

(56) References Cited

U.S. PATENT DOCUMENTS

| | | | | |
|---|---|---|---|---|
| 8,934,095 | B2 * | 1/2015 | Jung | G01J 3/513 356/402 |
| 2003/0011768 | A1 * | 1/2003 | Jung | G01J 3/0283 356/326 |
| 2003/0231309 | A1 * | 12/2003 | Fulghum, Jr. | A61B 5/0071 356/338 |
| 2009/0137893 | A1 * | 5/2009 | Seibel | A61B 1/00172 600/407 |
| 2011/0151409 | A1 * | 6/2011 | Binner | G01N 21/645 600/431 |
| 2013/0184555 | A1 * | 7/2013 | Chen | A61B 5/0088 600/407 |
| 2013/0197372 | A1 * | 8/2013 | Hijikuro | G01N 21/645 600/476 |
| 2015/0270945 | A1 * | 9/2015 | McMorrow | A61B 1/00165 398/154 |
| 2016/0038762 | A1 * | 2/2016 | Lin | A61N 5/0603 433/29 |
| 2024/0016425 | A1 * | 1/2024 | Sowards | A61B 1/00009 |
| 2025/0120590 | A1 * | 4/2025 | Son | A61B 5/0088 |
| 2025/0288089 | A1 * | 9/2025 | Berezhnoy | A46B 15/0004 |

FOREIGN PATENT DOCUMENTS

| | | | | | |
|---|---|---|---|---|---|
| CA | 2973128 | C | * | 7/2020 | A61B 1/00154 |
| CN | 111133285 | A | * | 5/2020 | G01J 3/0218 |
| CN | 117529272 | A | * | 2/2024 | A61B 5/0088 |
| JP | 10-309290 | A | | 11/1998 | |
| JP | 2005-324032 | A | | 11/2005 | |
| JP | 4576377 | B2 | * | 11/2010 | A61B 1/0605 |
| JP | 2011072719 | A | * | 4/2011 | |
| JP | 2013051999 | A | * | 3/2013 | |
| JP | 2023041120 | A | * | 3/2023 | A61B 5/0084 |
| KR | 10-2022-0067810 | A | | 5/2022 | |
| KR | 102700947 | B1 | * | 8/2024 | A61B 5/0088 |
| WO | WO-2023154667 | A2 | * | 8/2023 | A61B 5/4848 |
| WO | WO-2023208667 | A1 | * | 11/2023 | A61C 1/088 |

* cited by examiner

1

ORAL DIAGNOSTIC DEVICE USING LIGHT

CROSS-REFERENCE TO RELATED APPLICATION

This application claims priority from Korean Patent Application No. 10-2023-0138287 filed on Oct. 17, 2023, which is incorporated herein by reference in its entirety.

BACKGROUND

1. Technical Field

Embodiments of the present invention relate to a device for diagnosing a current condition of an oral cavity, including teeth, interdentals, gums, etc., using light.

2. Related Art

The consumption of food is one of the most important factors for humans, and in order to efficiently consume food, teeth and gums should be kept healthy. In order to maintain a healthy oral cavity, a user should brush his/her teeth properly and use dental floss.

In other words, when the user does not brush his/her teeth properly or does not use dental floss after consuming food, food residue remains on the teeth, which may proliferate bacteria and cause infectious diseases such as cavities. In addition, various minerals may be deposited, causing tartar, plaque, gum inflammation, etc. In particular, in the case of children, dental health may be often poor due to poor brushing of teeth, non-use of dental floss, etc.

In order to prevent the above-described oral diseases and keep teeth healthy, the user's oral condition should be measured periodically. Therefore, there is a need for a device that simply and easily checks the oral condition.

SUMMARY

It is an object of the present invention to provide a device for easily and accurately diagnosing a current condition of an oral cavity, including teeth, interdentals, gums, etc.

The objects of the present invention are not limited to the above-described objects, and other objects and advantages of the present invention that are not described may be understood by the following description and will be more clearly appreciated by exemplary embodiments of the present invention. In addition, it may be easily appreciated that aspects and advantages of the present invention may be realized by means mentioned in the claims and a combination thereof.

According to an embodiment of the present invention, an oral diagnostic device includes a device main body that includes an optical transmitting and receiving module, and a probe that is detachably coupled to the device main body, irradiates irradiated light received from the optical transmitting and receiving module into an oral cavity, receives reflected light from the irradiated light reflected from the oral cavity, and transmits the received reflected light to the optical transmitting and receiving device. In this case, the optical transmitting and receiving module includes an optical element module including a light-emitting element and a light-receiving element, a single first optical fiber that transmits the irradiated light generated by the light-emitting element to the probe, and a plurality of second optical fibers that transmit the reflected light received from the probe to the light-receiving element, and the other side of the single first optical fiber and the other side of the plurality of second optical fibers are coupled to each other to form an optical fiber coupling part.

According to the present invention, it is possible to easily and accurately diagnose the current condition of the oral cavity including teeth, interdentals, gums, etc.

In addition, it should be understood that the effects of the present invention are not limited to the above effects, and include all effects that can be inferred from the configuration of the invention described in the detailed description or claims of the present invention.

DETAILED DESCRIPTION

Figure 1:
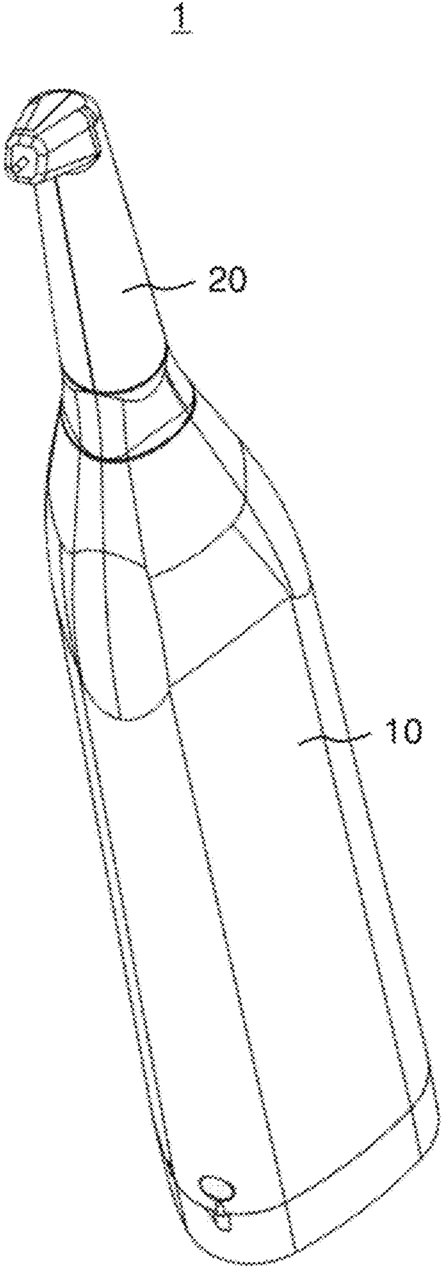
FIG. 1 is a perspective view of an oral diagnostic device according to an embodiment of the present invention.

The present invention may be variously modified and have several embodiments, and thus, specific embodiments will be illustrated in the drawings and be described in detail. However, it is to be understood that the present invention is not limited to a specific embodiment, but includes all modifications, equivalents, and substitutions without departing from the scope and spirit of the present invention. Throughout the drawings, similar components will be denoted by similar reference numerals.

The terms such as 'first', 'second', or the like, may be used to describe various components, but these components are not to be construed as being limited to these terms. The terms are used only for the purpose of distinguishing one component from another component. The term "and/or" includes a combination of a plurality of related described items or any one of the plurality of related described items.

It is to be understood that when one component is referred to as being "connected to" or "coupled to" another component, one component may be connected directly to or coupled directly to another component or be connected to or coupled to another component with the other component interposed therebetween. On the other hand, it is to be understood that when one component is referred to as being "connected directly to" or "coupled directly to" another component, it may be connected to or coupled to another component without the other component interposed therebetween.

The terms used in the present specification are used only for describing specific embodiments rather than limiting the present invention. Singular forms include plural forms unless the context clearly indicates otherwise. It is to be understood that the term "include" or "have" used herein specifies the presence of features, numbers, steps, operations, components, parts, or combinations thereof mentioned in the present specification, or combinations thereof, but does not preclude the presence or addition of one or more other features, numbers, steps, operations, components, parts, or combinations thereof.

Unless defined otherwise, it is to be understood that all the terms used in the specification including technical or scientific terms have the same meaning as those that are generally understood by those skilled in the art. The terms generally used and defined by a dictionary should be interpreted as having the same meanings as meanings within a context of the related art and should not be interpreted as having ideal or excessively formal meanings unless being clearly defined in the present specification.

Hereinafter, embodiments of the present invention will be described in detail with reference to the accompanying drawings.

Figure 2:
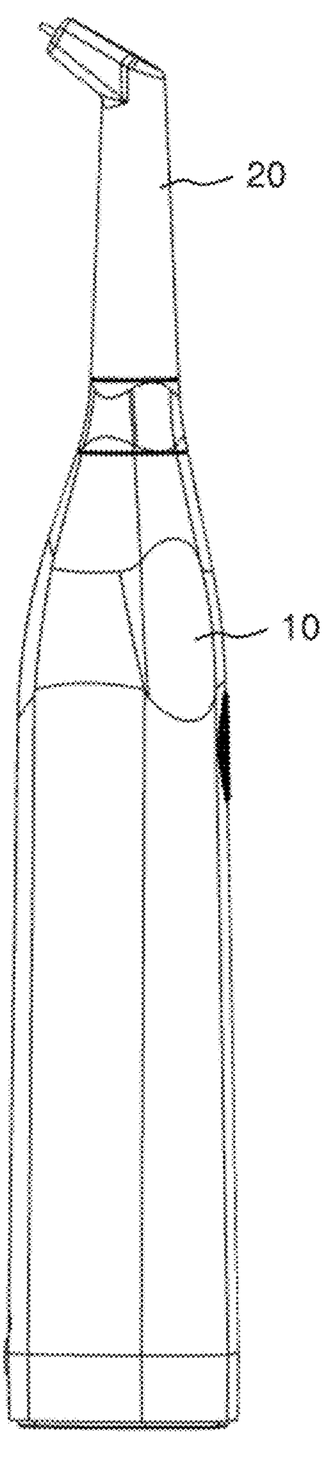
FIG. 2 is a front view of the oral diagnosis device according to the embodiment of the present invention.
Figure 3:
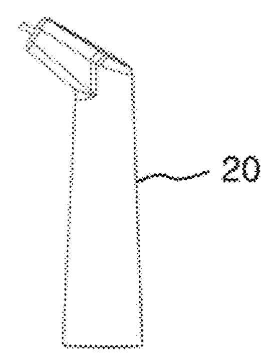
FIG. 3 is an exploded perspective view of the oral diagnosis device according to the embodiment of the present invention.
Figure 3:
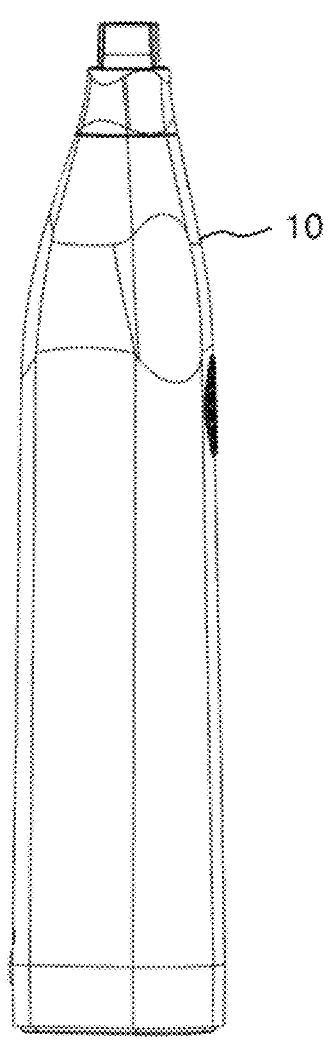
Figure 4A:
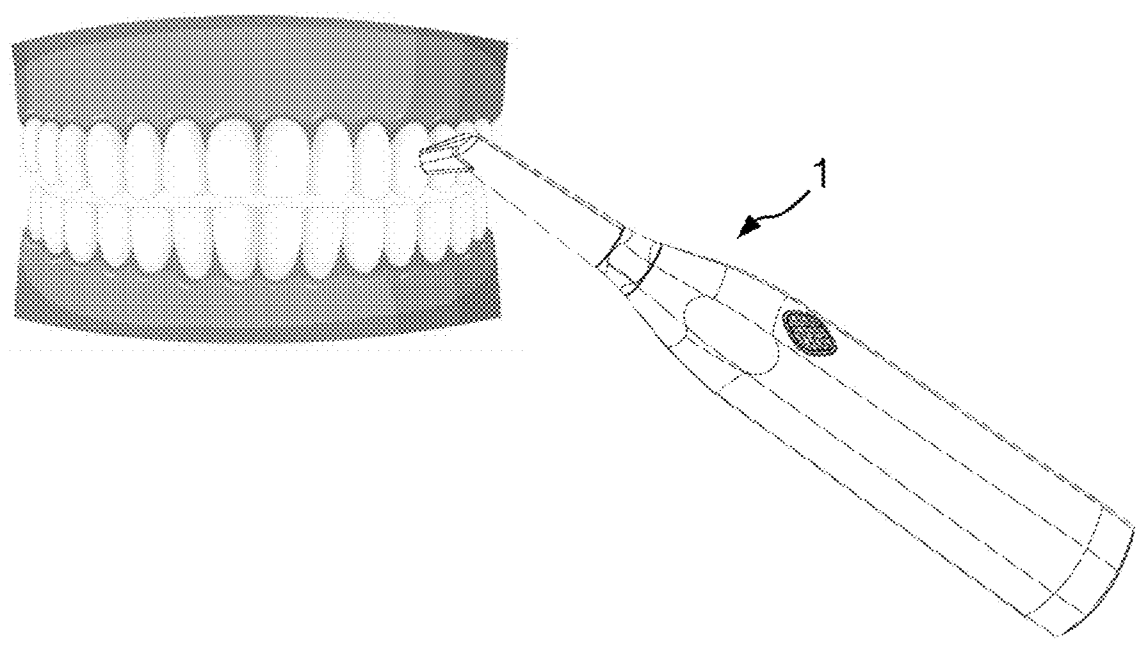
FIGS. 4A and 4B are diagrams illustrating a state in which the oral diagnosis device according to the embodiment of the present invention is used.
Figure 4B:
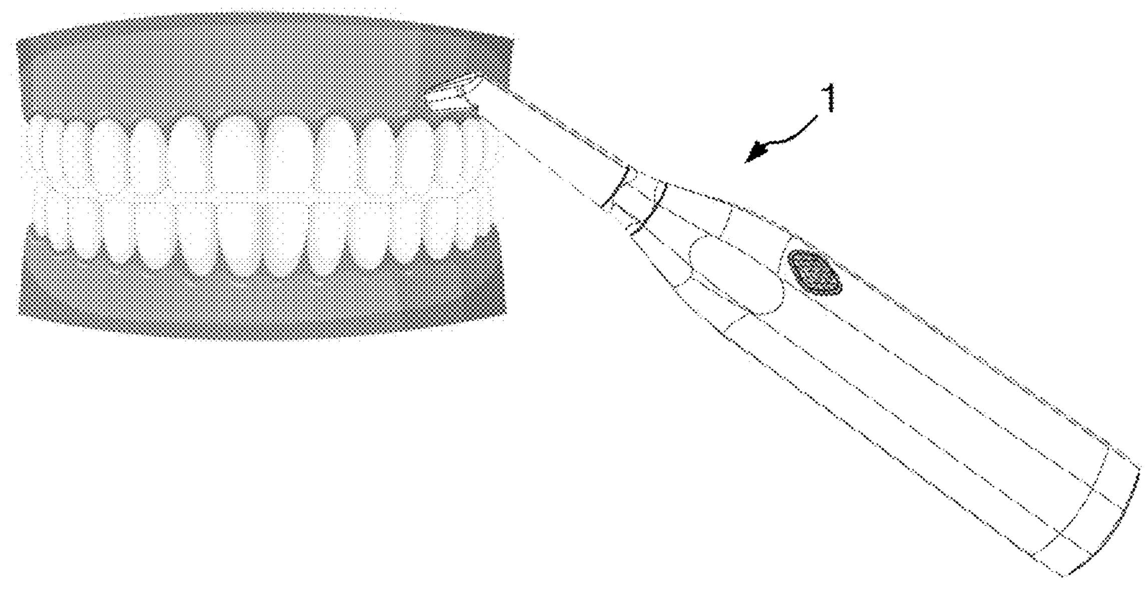

FIG. 1 is a perspective view of an oral diagnostic device 1 according to an embodiment of the present invention, FIG. 2 is a front view of the oral diagnosis device 1 according to the embodiment of the present invention, FIG. 3 is an exploded perspective view of the oral diagnosis device 1 according to the embodiment of the present invention, and FIGS. 4A and 4B are diagrams illustrating a state in which the oral diagnosis device 1 according to the embodiment of the present invention is used.

Referring to FIGS. 1 to 4B, the oral diagnostic device 1 according to an embodiment of the present invention may be a portable or mobile diagnostic device and may include a device main body 10 and a probe 20.

The device main body 10 is a main component of the oral diagnostic device 1, which generates light and may perform a function of diagnosing a condition of an oral cavity by analyzing light reflected from the oral cavity including teeth, gums, etc. As will be described later, in order to generate and receive light, the oral diagnostic device 1 may include an optical transmitting and receiving module 12 (FIGS. 5 to 8, and 10).

The probe 20 may be detachably coupled to the device main body 10, irradiate irradiated light generated and received from the optical transmitting and receiving module 12 to the oral cavity, and receive the reflected light from the irradiated light reflected from the oral cavity and transmit the received reflected light to the optical transmitting and receiving device 12. By being detachably coupled to the device main body 10, the probe 20 is replaceable.

Referring to FIGS. 4A and 4B, a user may hold the device main body 10 by hand and then allow the probe 20 to be disposed in contact with or very close to the teeth or gums. Accordingly, the oral diagnostic device 10 may diagnose or measure the condition of the oral cavity, such as the condition of the teeth or gums.

Hereinafter, the detailed configuration of the device main body 10 and the probe 20 will be described in more detail.

Figure 5:
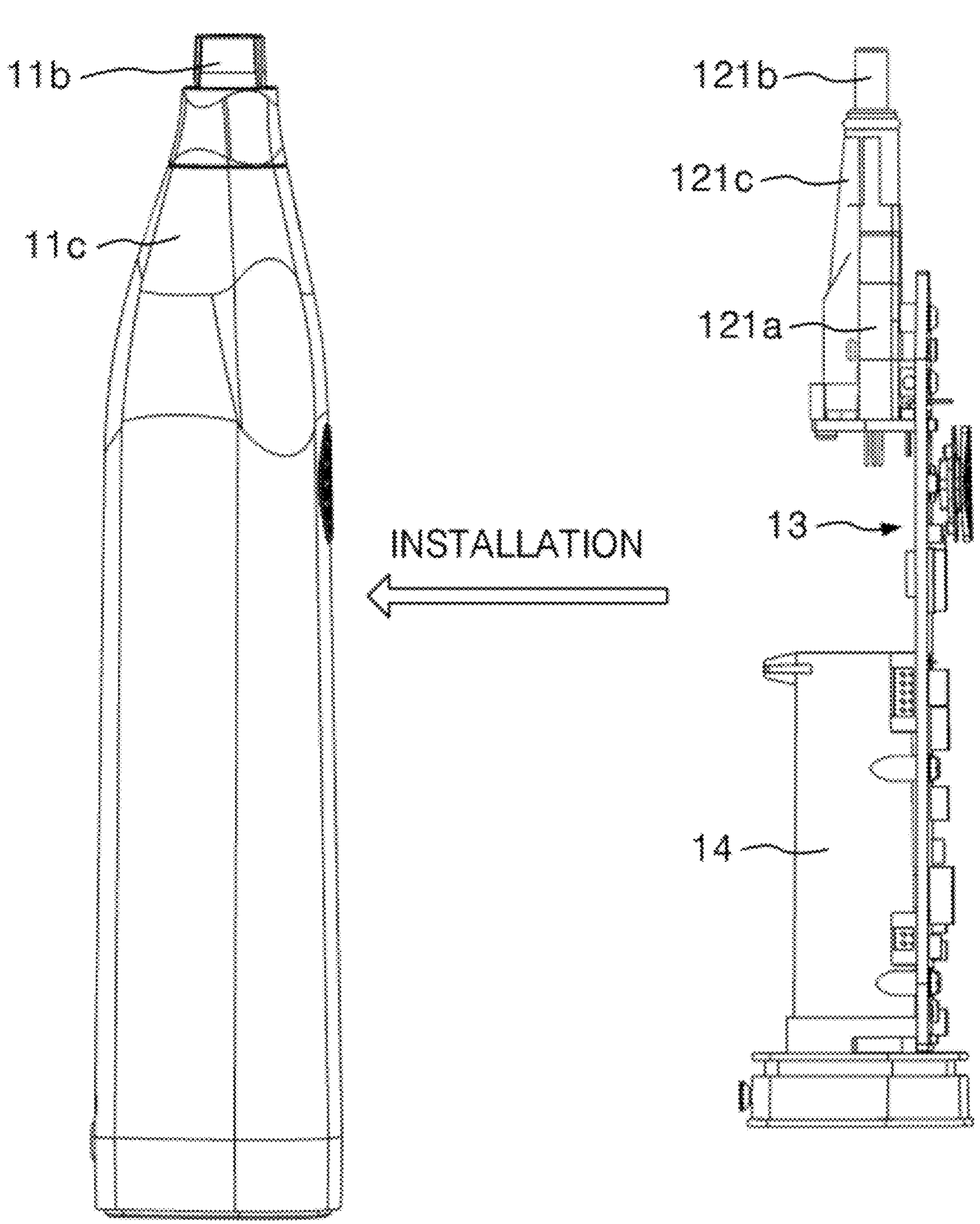
FIG. 5 is a diagram illustrating a detailed configuration of a device main body according to the embodiment of the present invention.

FIG. 5 is a diagram illustrating a detailed configuration of the device main body 10 according to the embodiment of the present invention.

Referring to FIG. 5, the device main body 10 may include a main body case 11, an optical transmitting and receiving module 12, a PCB module 13, and a battery module 14.

The main body case 11 may form the overall appearance of the device main body 10. The main body case 11 has an internal space, and the optical transmitting and receiving module 12, the PCB module 13, and the battery module 14 may be installed or accommodated in the internal space of the main body case 11.

The main body case 11 may include a first portion 11*a*, a second portion 11*b*, and a third portion 11*c*.

The first portion 11*a* of the main body case 11 may be held by the user's hand. A portion of the PCB module 13 and the battery module 14 may be accommodated in the internal space of the main body case 11 corresponding to the first portion 11*a* of the main body case 11.

A second portion 11*b* of the main body case 11 may be detachably coupled to the probe 20. A third portion 11*c* of the main body case 11 may connect the first portion 11*a* and the second portion 11*b* of the main case 11. The optical transmitting and receiving module 12 and the remaining portion of the PCB module 13 may be accommodated in the internal space of the main body case 11 corresponding to the second portion 11*b* and the third portion 11*c* of the main body case 11.

Figure 8:
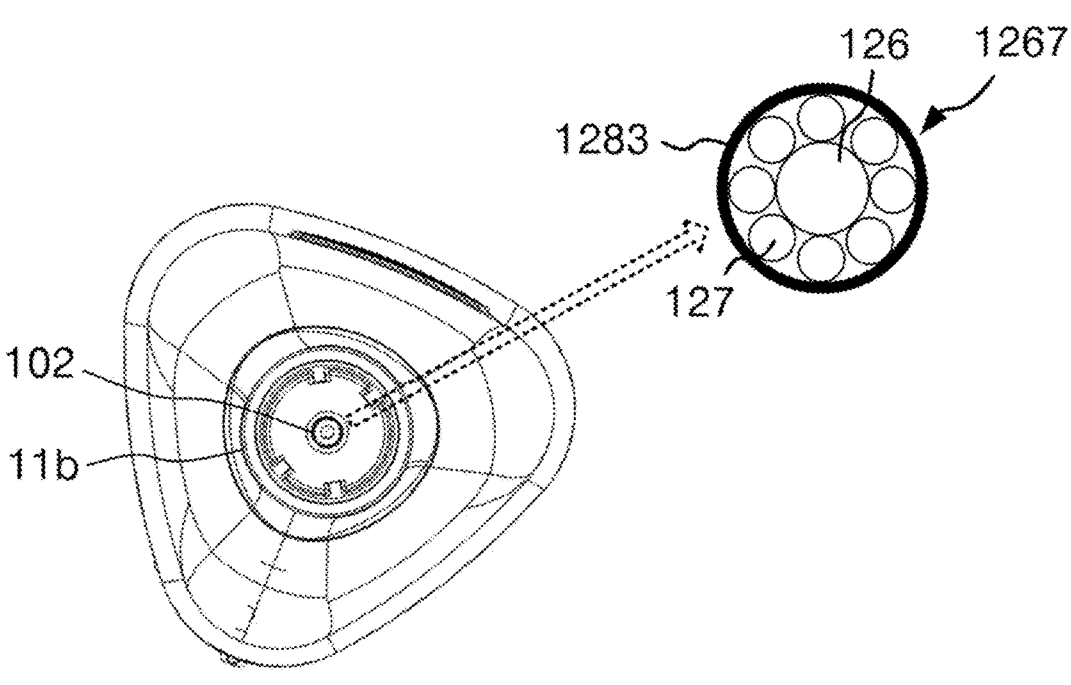
FIG. 8 is a diagram illustrating a plan shape of the optical transmitting and receiving module installed in a main body case according to an embodiment of the present invention.

The second portion 11*b* of the main body case 11 may be formed to protrude from the first portion 11*a* of the main body case 11 through the third portion 11*c* of the main body case 11. Referring to FIG. 8, which will be described later, an opening 102 may be formed on an upper surface (one side surface) of the second portion 11*b* of the main body case 11.

The first portion 11*c* of the main body case 11 may generally have a shape of a triangular pillar. The third portion 11*c* of the main body case 11 may generally have a shape of a triangular pyramid. That is, corners constituting the outer surface of the third portion 11*c* of the main case 11 may be formed to be inclined at a specific angle.

The optical transmitting and receiving module 12 may generate the irradiated light and transmit the generated irradiated light to the probe 20, and detect the reflected light received from the probe 20 and transmit the detected reflected light to the PCB module 13. The detailed shape of the optical transmitting and receiving module 12 will be described later.

The PCB module 13 may control the optical transmitting and receiving module 12. In particular, the PCB module 13 may analyze the reflected light to diagnose or measure the oral cavity condition. The PCB module 13 may be configured to include a processor, a communication unit, etc. The PCB module 13 may transmit the diagnosed oral cavity condition to the user's terminal device, for example, a smart device through the communication unit.

The battery module 14 may supply driving power to the optical transmitting and receiving module 12 and the PCB module 13. The battery module 14 may be configured to include a dry cell and a battery compartment, or may be a battery that can be recharged using commercial power.

Hereinafter, the optical transmitting and receiving module 12 will be described in more detail.

Figure 6:
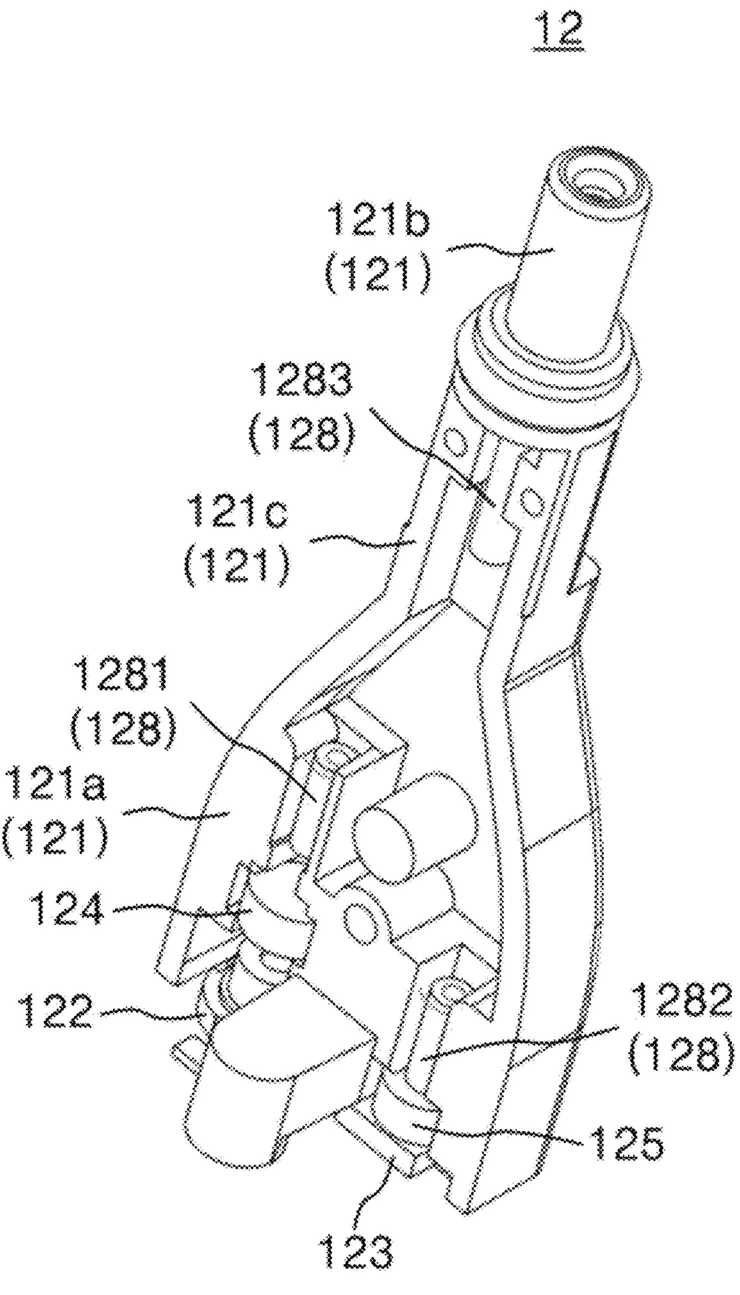
FIG. 6 is a perspective view of an optical transmitting and receiving module according to an embodiment of the present invention.
Figure 7:
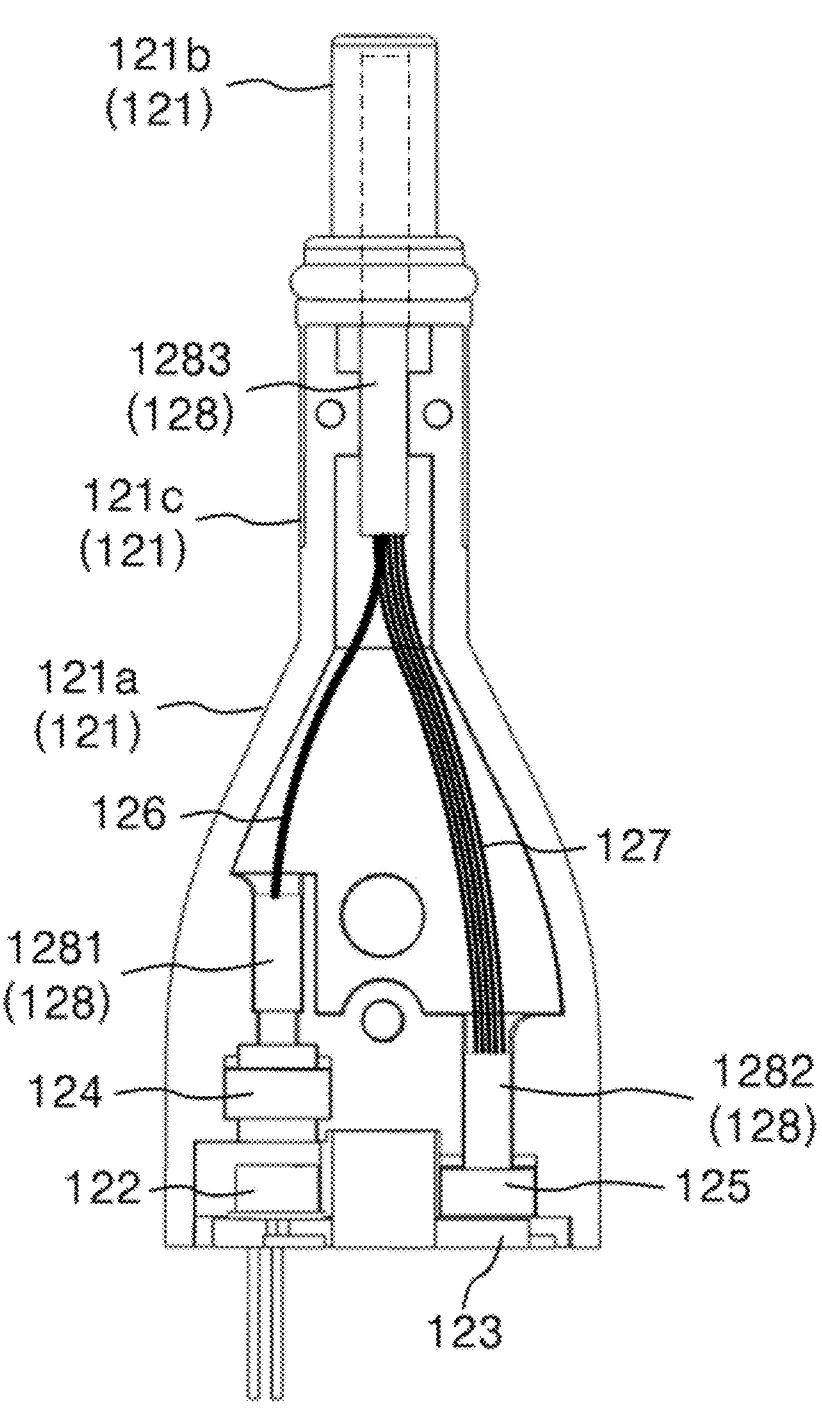
FIG. 7 is a cross-sectional view of the optical transmission/reception module according to the embodiment of the present invention.

FIG. 6 is a perspective view of the optical transmitting and receiving module 12 according to an embodiment of the present invention, FIG. 7 is a cross-sectional view of the optical transmission/reception module 12 according to the embodiment of the present invention, and FIG. 8 is a diagram illustrating a plan shape of the optical transmitting and receiving module 12 installed in the main body case 11 according to an embodiment of the present invention. Meanwhile, for convenience of description, some components included in the optical transmitting and receiving module 12 are omitted in FIG. 6.

Referring to FIGS. 6 and 8, the optical transmitting and receiving module 12 may include a module case 121, a light-emitting element 122, a light-receiving element 123, a first lens 124, a second lens 125, a single first optical fiber 126, a plurality of second optical fibers 127, and an optical fiber tube 128. The light-emitting element 122 and the light-receiving element 123 may constitute optical element modules 122 and 123, and the optical fiber may also be called an optical cable.

The module case 121 may configure the exterior of the optical transmitting and receiving module 12. The module case 121 has an internal space, and optical element modules 122 and 123, a lens 124, an optical filter 125, a single first optical fiber 126, a plurality of second optical fibers 127, and an optical fiber tube 128 may be installed or accommodated in the internal space of the module case 121.

The module case 121 may include a first portion 121*a*, a second portion 121*b*, and a third portion 121*c*.

The optical element modules 122 and 123, one side of the single first optical fiber 126, and one side of the plurality of second optical fibers 127 may be disposed in the first portion 121*a* of the module case 121. The first portion 121*a* of the module case 121 may have both side surfaces of a convex curved shape. Referring to FIG. 5, the first portion 121*a* of the module case 121 may be accommodated in the third portion 11*c* of the main body case 11. In particular, since the third portion 11*c* of the main body case 11 has a shape of a triangular pyramid, the first portion 121*a* of the module case 121, which has both side surfaces of the convex curved shape, may be easily accommodated.

The second portion 121*b* of the module case 121 may be a portion of the module case 121 coupled to the probe 20, and the other side of the single first optical fiber 126 and the other side of the plurality of second optical fibers 127 may be disposed. Referring to FIG. 8, the other side of the single first optical fiber 126 and the other side of the plurality of second optical fibers 127 may be coupled to each other by an adhesive or the like to form an optical fiber coupling part 1267, and the optical fiber coupling part 1267 may be accommodated in the second portion 121*b* of the module case 121. The second portion 121*b* of the module case 121 may have a cylindrical shape.

Referring to FIGS. 5 and 8, the second portion 121*b* of the module case 121 may be accommodated in the second portion 11*b* of the main body case 11. In particular, an upper surface of the second portion 121*b* of the module case 121 may be disposed directly below the opening 102 formed in the second portion 11*b* of the main body case 11.

The third portion 121*c* of the module case 121 may connect the first portion 121*a* and the second portion 11*b* of the module case 121. A middle side of the single first optical fiber 126 and a middle side of the plurality of second optical fibers 127 may be disposed in the third portion 121*c* of the module case 121. The third portion 121*c* of the module case 121 may have a cylindrical shape. The second portion 121*b* of the module case 121 may be formed to protrude from the first portion 121*a* of the module case 121 through the third portion 121*c* of the main body case 121.

The light-emitting element 122 may generate the irradiated light. The light-emitting element 122 may be disposed along a first side surface of the first portion 121*a* of the module case 121. For example, the light-emitting element may be a laser diode that converts an electrical signal into light.

The light-receiving element 123 may detect the reflected light. The light-receiving element 123 may be disposed along a second side surface of the first portion 121*a* of the module case 121. For example, the light-receiving element 123 may be a photodiode that converts light into an electrical signal.

The lens 124 may focus the irradiated light generated from the light-emitting element 122. The lens 124 may be disposed along the first side surface of the first portion 121*a* of the module case 121.

The optical filter 125 may be a device that selectively transmits or prevents a band of a certain wavelength from being transmitted among the incident reflected light. The optical filter 125 may be disposed along the second side surface of the first portion 121*a* of the module case 121.

The single first optical fiber 126 may transmit the irradiated light generated by the light-emitting element 122 to the probe 20. One side of the single first optical fiber 126 may be disposed on the light-emitting element 122 side, and the other side of the single first optical fiber 126 may be disposed on the probe 20 side. One side of the single first optical fiber 126 may be disposed along the first side surface of the first portion 121*a* of the module case 121. Each of one side and the other side of the single first optical fiber 126 may be accommodated in a first optical fiber tube 1281 and a third optical fiber tube 1283, so the disconnection, etc., may be prevented.

The plurality of second optical fibers 127 may transmit the reflected light received by the probe 20 to the light-receiving element 123. For example, the number of second optical fibers 127 may be eight. One side of the plurality of second optical fibers 127 may be disposed on the light-emitting element 123 side, and the other side of the plurality of second optical fibers 127 may be disposed on the probe 20 side. One side of the plurality of second optical fibers 127 may be disposed along the second side surface of the first portion 121*a* of the module case 121. Each of one side and the other side of the plurality of second optical fibers 127 may be accommodated in a second optical fiber tube 1282 and a third optical fiber tube 1283, so the disconnection, etc., may be prevented.

According to an embodiment, the cross-section of the single first optical fiber 126 and the plurality of second optical fibers 127 may be circular, and the size (i.e., diameter) of the single first optical fiber 126 may be larger than that of each of the plurality of second optical fibers 127. For example, the size of the single first optical fiber 126 may be 0.5 π, and the size of each of the plurality of second optical fibers 127 may be 0.25 π.

According to an embodiment, one side of the single first optical fiber 126 and one side of the plurality of second optical fibers 127 may be disposed in a curved shape along both side surfaces of the first portion 121*a* of the module case 121. By disposing one side of the single first optical fiber 126 and the plurality of second optical fibers 127 in the curved shape, a transmission loss of the irradiated light and reflected light may be minimized. Meanwhile, in order to easily dispose one side of the single first optical fiber 126 and the plurality of second optical fibers 127 in the curved shape inside the optical transmitting and receiving module 12, the first portion 121*a* of the module case 121 may be formed to have both side surfaces in a convex curved shape.

As described above, referring to FIG. 8, the other side of the single first optical fiber 126 and the other side of the plurality of second optical fibers 127 are coupled to each other inside the third optical fiber tube 1283, so an optical fiber coupling part 1267 may be formed.

According to an embodiment, the optical fiber coupling part 1267 may be composed of a center area and an edge area. The single first optical fiber 126 may be disposed in the center area of the optical fiber coupling part 1267, and the plurality of second optical fibers 127 may be disposed in the edge area of the optical fiber coupling part 1267. In particular, the plurality of second optical fibers 127 may be disposed to surround the single first optical fiber 126.

Hereinafter, the probe 20 will be described in more detail.

Figure 9:
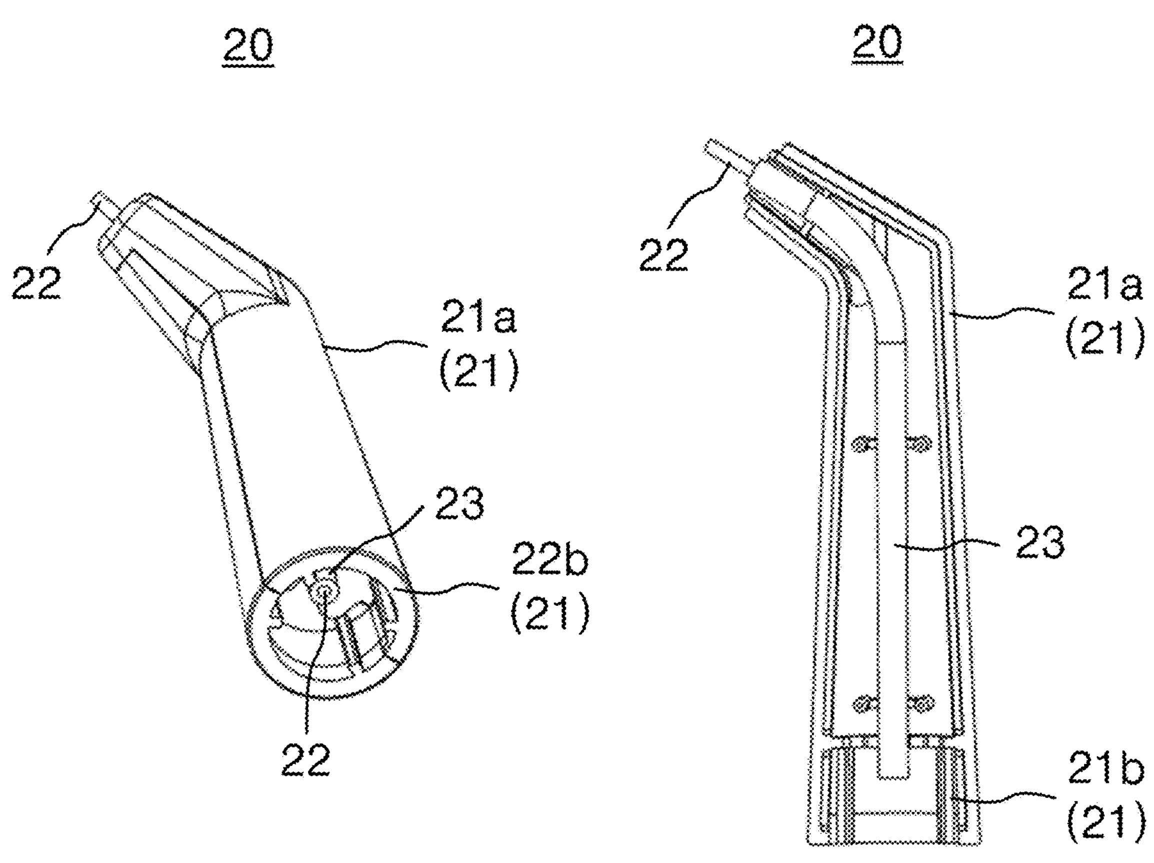
FIG. 9 is a perspective view of a probe according to an embodiment of the present invention.
Figure 10:
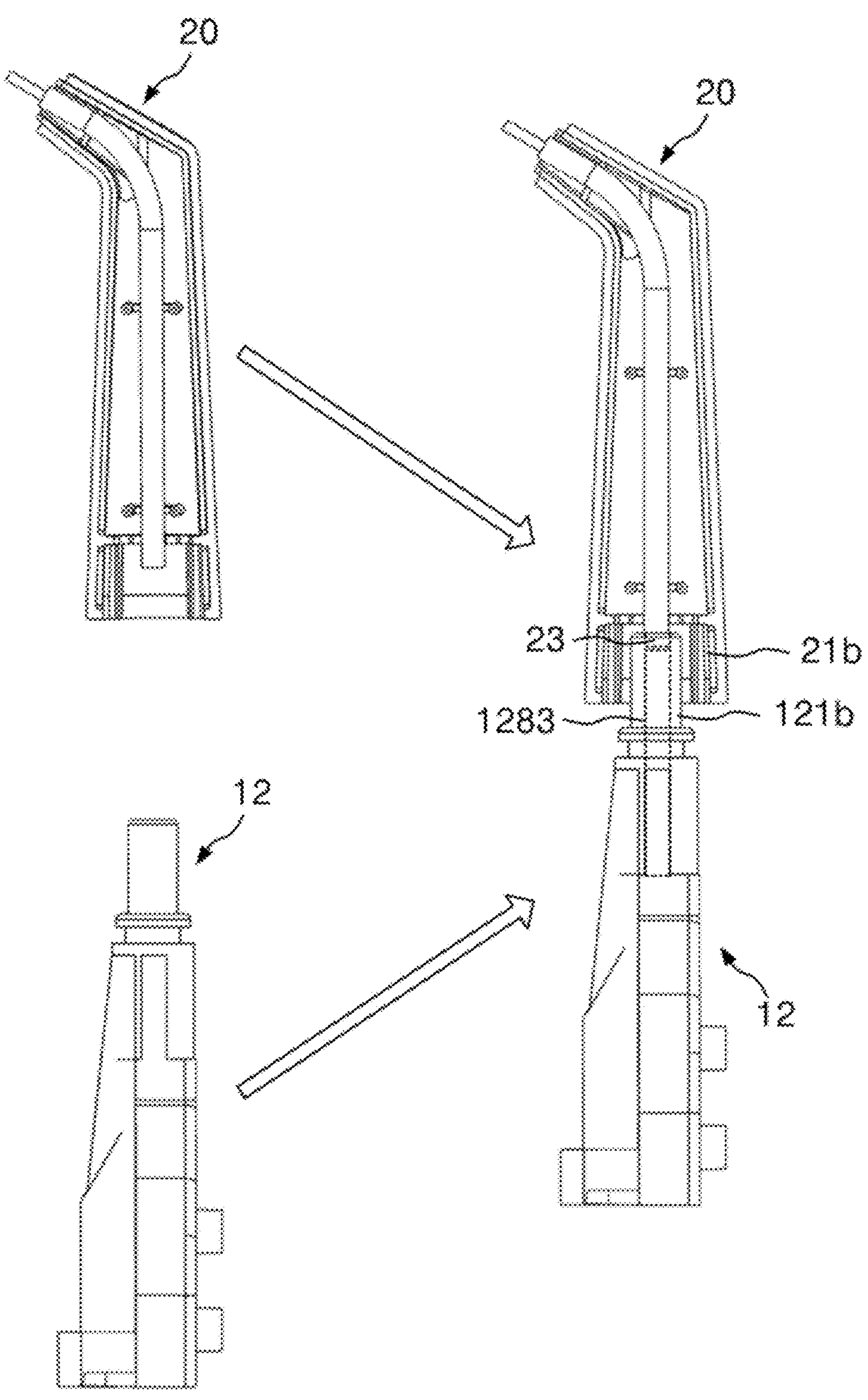
FIG. 10 is a diagram illustrating a combined shape of the optical transmitting and receiving module and the probe according to the embodiment of the present invention.

FIG. 9 is a perspective view of the probe 20 according to an embodiment of the present invention, and FIG. 10 is a diagram illustrating a combined shape of the optical transmitting and receiving module 12 and the probe 20 according to the embodiment of the present invention. Meanwhile, for convenience of description, the shape of the main body case 11 is omitted in FIG. 10.

Referring to FIG. 9, the probe 20 may include a probe case 21, a single third optical fiber 22, and a covering member 23.

The probe case 21 may configure the exterior of the probe 20. The probe case 21 has an internal space, and the single third optical fiber 22 may be accommodated in the internal space of the probe case 21.

The single third optical fiber 22 may irradiate the irradiated light received from the optical transmitting and receiving module 12 to the oral cavity, and receive reflected light from the irradiated light reflected from the oral cavity.

According to an embodiment, the cross-section of the single third optical fiber 22 may be circular, and the size (i.e., diameter) of the single third optical fiber 22 may be larger than that of the single first optical fiber 126 and that of each of the plurality of second optical fibers 127. As an example, the size of the single third optical fiber 22 may be 1.0 $\pi$.

Meanwhile, the probe case 21 may include a first portion 21*a* and a second portion 21*b*.

The middle side of the single third optical fiber 22 may be accommodated in the first portion 21*a* of the probe case 21.

One side of the single third optical fiber 22 may be accommodated in the second portion 21*b* of the probe case 21. Here, one side of the single third optical fiber 22 may be disposed to protrude from a portion of the internal space of the second portion 21*b* of the probe case 21. Referring to FIG. 10, one side of the single third optical fiber 22 may be disposed adjacent to the optical fiber coupling part 1256.

The other side of the single third optical fiber 22 may be disposed to protrude outward from the first portion 21*a* of the probe case 21. The other side of the single third optical fiber 22 may irradiate the irradiated light to the oral cavity and receive the reflected light reflected from the oral cavity.

The covering member 23 may be formed to surround one side and the middle side of the single third optical fiber 22 and protect one side and the middle side of the single third optical fiber 22.

Referring to FIG. 10, the second portion 21*b* of the probe case 21 may have the internal space corresponding to the shape of the second portion 11*b* of the main case 11. Accordingly, an inner surface of the second portion 21*b* of the probe case 21 is coupled with an outer surface of the second portion 11*b* of the main case 11 in the fitting shape, so the probe 20 may be coupled to the main case 11.

Referring to FIG. 10, when the probe 20 is not coupled to the second portion 11*b* of the main body case 11, one side of the single third optical fiber 22 may be disposed to protrude from the internal space of the second portion 21*b* of the probe case 21. Alternatively, when the probe 20 is coupled with the second portion 11*b* of the main body case 11, one side of the single third optical fiber 22 may pass through the opening 102 to be disposed adjacent to the optical fiber coupling part 1256 inside the second portion of the main body case 11.

In summary, the oral diagnostic device 1 according to an embodiment of the present invention may diagnose the condition of the oral cavity by transmitting and receiving light, for example, a laser, to the oral cavity. In this case, the optical fiber coupling part 1267 may be formed so that the single first optical fiber 126 transmitting the irradiated light is disposed in the center, and the plurality of second optical fibers 127 transmitting the reflected light are disposed at the edge. For an example, the plurality of second optical fibers 127 may be disposed in a circular shape with the single first optical fiber 126 as the center. In addition, the size of each of the plurality of second optical fibers 127 may be formed to be smaller than that of the single first optical fiber 126. Accordingly, the reflected light reflected from the diagnosis object (teeth, gums) may be received without exception, so the oral cavity condition of the diagnosis object may be accurately diagnosed without error.

Hereinabove, although the present invention has been described by specific matters such as detailed components, limited exemplary embodiments, and the accompanying drawings, it is provided only for assisting in the entire understanding of the present invention. Therefore, the present invention is not limited to the exemplary embodiments. Various modifications and changes may be made by those skilled in the art to which the present invention pertains from this description. Therefore, the spirit of the present invention should not be limited to these exemplary embodiments, but the claims and all of modifications equal or equivalent to the claims are intended to fall within the scope and spirit of the present invention.

What is claimed is:

1. An oral diagnostic device, comprising:

a device main body that includes an optical transmitting and receiving module; and a probe that is detachably coupled to the device main body, irradiates irradiated light received from the optical transmitting and receiving module into an oral cavity, receives reflected light from the irradiated light reflected from the oral cavity, and transmits the received reflected light to the optical transmitting and receiving device, wherein the optical transmitting and receiving module includes an optical element module including a light-emitting element and a light-receiving element, a single first optical fiber that transmits the irradiated light generated by the light-emitting element to the probe, and a plurality of second optical fibers that transmit the reflected light received from the probe to the light-receiving element, wherein a distal side of the single first optical fiber and a distal side of the plurality of second optical fibers are coupled to each other to form an optical fiber coupling part, wherein the device main body includes a main body case that accommodates the optical transmitting and receiving module, the main body case comprising:

a first portion configured to be held by a user; and a second portion that protrudes from the first portion of the main body case, wherein the optical transmitting and receiving module includes a module case that accommodates the optical element module, the single first optical fiber, and the plurality of second optical fibers, the module case comprising:

a first portion in which the optical device module, the proximal side of the single first optical fiber, and the proximal side of the plurality of second optical fibers are disposed; and a second portion in which the optical fiber coupling part is disposed, wherein the probe includes:

a probe case;

a single third optical fiber accommodated in the probe case, wherein a proximal side of the single third optical fiber is configured to be disposed adjacent to the optical fiber coupling part when the probe is coupled to the device main body, and a distal side of the single third optical fiber protrudes from the probe case and irradiates the irradiation light and receives the reflected light; and a covering member that surrounds the proximal side and a middle portion of the single third optical fiber, wherein the probe case includes:

a first portion that accommodates the middle portion of the single third optical fiber; and a second portion that accommodates the proximal side of the single third optical fiber and has an internal space corresponding to a shape of the second portion of the main body case, and wherein, when the probe is coupled to the device main body, the second portion of the probe case is detachably coupled to the second portion of the main body case, and a proximal end of the covering member is inserted into a distal end of the second portion of the module case and is disposed adjacent to the optical fiber coupling part inside the second portion of the module case.

2. The oral diagnostic device of claim 1, wherein the proximal side of the single first optical fiber is disposed on the light-emitting element side, and the proximal side of each of the plurality of second optical fibers is disposed on the light-receiving element side.

3. The oral diagnostic device of claim 1, wherein the optical fiber coupling part is composed of a central area where the single first optical fiber is disposed and an edge area where the plurality of second optical fibers are disposed.

4. The oral diagnostic device of claim 3, wherein a size of each of the plurality of second optical fibers is smaller than that of the single first optical fiber, and wherein a diameter of the single third optical fiber is larger than that of the single first optical fiber and that of the plurality of second optical fibers.

5. The oral diagnostic device of claim 4, wherein each of the single first optical fiber, the plurality of second optical fibers, and the single third optical fiber has a circular cross-section, wherein the diameter of the single first optical fiber is 0.5 mm, wherein the diameter of each of the plurality of second optical fibers is 0.25 mm, and wherein the diameter of the single third optical fiber is 1.0 mm.

6. The oral diagnostic device of claim 1, wherein the first portion of the module case has a curved shape such that the first portion of the module case is widened going toward the device main body, and wherein the proximal side of the single first optical fiber and the proximal side of the plurality of second optical fibers are disposed in a curved shape along both sides of the first portion of the module case.

7. The oral diagnostic device of claim 1, wherein the first portion of the module case is disposed inside the first portion of the main body case, and wherein the second portion of the module case is disposed inside the second portion of the main body case, and the probe is coupled to an outer surface of the second portion of the main body case.

8. The oral diagnostic device of claim 1, wherein the distal side of the single third optical fiber protrudes from the first portion of the probe case, and wherein the second portion of the probe case is coupled to the second portion of the main body case in a fitting shape.

9. The oral diagnostic device of claim 1, wherein an opening is formed on a distal side surface of the second portion of the main body case, wherein, when the probe is decoupled from the second portion of the main body case, the proximal side of the single third optical fiber is disposed within the internal space of the second portion of the probe case, and wherein, when the probe is coupled to the second portion of the main body case, the proximal side of the single third optical fiber passes through the opening and is disposed adjacent to the optical fiber coupling part inside the second portion of the main body case.

* * * * *